US00PP19172P2

(12) United States Plant Patent
Hofmann

(10) Patent No.: US PP19,172 P2
(45) Date of Patent: Sep. 2, 2008

(54) **NEW GUINEA *IMPATIENS* PLANT NAMED 'FISNICS SALICE'**

(50) Latin Name: *Impatiens hawkeri*
Varietal Denomination: Fisnics Salice

(76) Inventor: Birgit Hofmann, Gassenweg 29, 56170 Bendorf (DE)

( * ) Notice: Subject to any disclaimer, the term of this patent is extended or adjusted under 35 U.S.C. 154(b) by 0 days.

(21) Appl. No.: 11/800,778

(22) Filed: May 7, 2007

(51) Int. Cl.
*A01H 5/00* (2006.01)

(52) U.S. Cl. ..... Plt./318.1

(58) Field of Classification Search ..... Plt./318.1
See application file for complete search history.

*Primary Examiner*—Annette H Para
(74) *Attorney, Agent, or Firm*—C. A. Whealy

(57) ABSTRACT

A new and distinct cultivar of *Impatiens* plant named 'Fisnics Salice', characterized by its upright and outwardly spreading growth habit; mounded plant habit; freely branching habit; moderately vigorous growth habit; dark green-colored leaves; freely flowering habit; large salmon pink and white bi-colored flowers; and good garden performance.

1 Drawing Sheet

Botanical designation: *Impatiens hawkeri.*
Cultivar denomination: 'Fisnics Salice'.

BACKGROUND OF THE INVENTION

The present invention relates to a new and distinct cultivar of New Guinea *Impatiens,* botanically known as *Impatiens hawkeri* and hereinafter referred to by the name 'Fisnics Salice'.

The new *Impatiens* is a product of a planned breeding program conducted by the Inventor in Hillscheid, Germany. The objective of the breeding program is to create new freely-branching and moderately vigorous New Guinea *Impatiens* cultivars with large and attractive flowers.

The new *Impatiens* originated from a cross-pollination made by the Inventor during the summer of 2002 in Hillscheid, Germany of a proprietary selection of *Impatiens hawkeri* identified as code number K02-9114-1, not patented, as the female, or seed, parent with a proprietary selection of *Impatiens hawkeri* identified as code number K01-8593-2, not patented, as the male, or pollen, parent. The new *Impatiens* was discovered and selected by the Inventor as a single flowering plant within the progeny of the stated cross-pollination in a controlled environment in Moncarapacho, Portugal in March, 2003.

Asexual reproduction of the new *Impatiens* by terminal cuttings in a controlled environment in Moncarapacho, Portugal since June, 2003, has shown that the unique features of this new *Impatiens* are stable and reproduced true to type in successive generations.

SUMMARY OF THE INVENTION

The cultivar Fisnics Salice has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fisnics Salice'. These characteristics in combination distinguish 'Fisnics Salice' as a new and distinct cultivar of *Impatiens:*

1. Upright and outwardly spreading growth habit; mounded plant habit.
2. Freely branching habit.
3. Moderately vigorous growth habit.
4. Dark green-colored leaves.
5. Freely flowering habit.
6. Large salmon pink and white bi-colored flowers.
7. Good garden performance.

Plants of the new *Impatiens* can be compared to plants of the female parent selection. Plants of the new *Impatiens* differ primarily from plants of the female parent selection in leaf and flower color as plants of the female parent selection have lighter green-colored leaves and light red-colored flowers.

Plants of the new *Impatiens* can be compared to plants of the male parent selection. Plants of the new *Impatiens* differ primarily from plants of the male parent selection in flower color as plants of the male parent selection have darker salmon pink-colored flowers. In addition, plants of the male parent selection have a more open plant habit and longer internodes than plants of the new *Impatiens.*

Plants of the new *Impatiens* can be compared to plants of the *Impatiens* cultivar Fisnics Salmon Ice, disclosed in U.S. Plant Pat. No. 14,812. In side-by-side comparisons conducted in Hillscheid, Germany, plants of the new *Impatiens* differed from plants of the cultivar Fisnics Salmon Ice in the following characteristics:

1. Plants of the new *Impatiens* were larger than plants of the cultivar Fisnics Salmon Ice.
2. Plants of the new *Impatiens* had darker green-colored leaves than plants of the cultivar Fisnics Salmon Ice.
3. Plants of the new *Impatiens* had larger flowers than plants of the cultivar Fisnics Salmon Ice.
4. Plants of the new *Impatiens* and the cultivar Fisnics Salmon Ice differed in flower color.

Plants of the new *Impatiens* can be compared to plants of the *Impatiens* cultivar Fisupnic Salice, disclosed in U.S. Plant patent application Ser. No. 11/330,838, abandoned. In side-by-side comparisons conducted in Hillscheid, Germany, plants of the new *Impatiens* differed from plants of the cultivar Fisupnic Salice in the following characteristics:

1. Plants of the new *Impatiens* were smaller than plants of the cultivar Fisupnic Salice.
2. Plants of the new *Impatiens* were less vigorous than plants of the cultivar Fisupnic Salice.
3. Plants of the new *Impatiens* and the cultivar Fisupnic Salice differed in flower color.

BRIEF DESCRIPTION OF THE PHOTOGRAPHS

The accompanying colored photographs illustrate the overall appearance of the new *Impatiens,* showing the colors as true as it is reasonably possible to obtain in colored reproductions of this type. Colors in the photographs may differ slightly from the color values cited in the detailed botanical description which accurately describe the colors of the new *Impatiens*.

The photograph at the top of the sheet comprises a side perspective view of typical flowering plants of 'Fisnics Salice' grown in a container.

The photograph at the bottom of the sheet is a close-up view of a typical flower of 'Fisnics Salice'.

DETAILED BOTANICAL DESCRIPTION

The aforementioned photographs and following observations, measurements and values describe plants grown in Hillscheid, Germany, in containers and under commercial practice during the spring in a glass-covered greenhouse with day temperatures ranging from 16° C. to 22° C. and night temperatures averaging about 16° C. Rooted young plants had been growing for about ten to twelve weeks when the photograph and description were taken. In the following description, color references are made to The Royal Horticultural Society Colour Chart, 2001 Edition, except where general terms of ordinary dictionary significance are used.

Botanical classification: *Impatiens hawkeri* cultivar Fisnics Salice.

Parentage:

*Female, or seed, parent.*—Proprietary selection of *Impatiens hawkeri* identified as code number K02-9114-1, not patented.

*Male, or pollen, parent.*—Proprietary selection of *Impatiens hawkeri* identified as code number K01-8593-2, not patented.

Propagation:

*Type.*—By terminal cuttings.

*Time to initiate roots, summer.*—About ten days at temperatures of 22° C. to 24° C.

*Time to initiate roots, winter.*—About 14 days at temperatures of 20° C. to 22° C.

*Time to produce a rooted young plant, summer.*—About 18 days at temperatures of 22° C. to 24° C.

*Time to produce a rooted young plant, winter.*—About 21 days at temperatures of 20° C. to 22° C.

*Root description.*—Fine, fibrous; dull to creamy white in color.

*Rooting habit.*—Freely branching; moderately dense.

Plant description:

*Plant and growth habit.*—Upright to outwardly spreading growth habit; mounded plant habit. Freely branching habit with about six lateral branches; pinching is typically not required. Moderately vigorous growth habit.

*Plant height.*—About 11.3 cm.

*Plant diameter.*—About 21 cm.

Lateral branch description:

*Length.*—About 8 cm to 11 cm.

*Diameter.*—About 6 mm to 8 mm.

*Internode length.*—About 2.5 cm.

*Strength.*—Strong.

*Aspect.*—Initially upright to outwardly spreading.

*Texture.*—Smooth, glabrous.

*Color.*—181A to 181B; towards the apex, 53A.

Foliage description:

*Arrangement.*—Typically in whorls; simple.

*Length.*—About 11.5 cm.

*Width.*—About 4 cm.

*Shape.*—Elliptical.

*Apex.*—Acuminate.

*Base.*—Attenuate.

*Margin.*—Slightly serrulate with ciliation.

*Texture, upper and lower surfaces.*—Smooth, glabrous; leathery; slightly rugose.

*Venation pattern.*—Pinnate; arcuate.

*Color.*—Developing foliage, upper surface: 137B to 137C. Developing foliage, lower surface: 138B. Fully expanded foliage, upper surface: 137A; venation, close to 51B. Fully expanded foliage, lower surface: 139C; venation, 53C.

*Petiole length.*—About 1 cm.

*Petiole diameter.*—About 4 mm.

*Petiole texture, upper and lower surfaces.*—Smooth, glabrous.

*Petiole color, upper and lower surfaces.*—53C to 53D.

Flower description:

*Flower type and flowering habit.*—Single rounded axillary flowers. Freely flowering habit; usually about five to nine open flowers and flower buds per lateral branch. Flowers positioned above the foliage and typically face upright or outward. Flowers last about one week under greenhouse conditions. Petals self-cleaning, gynoecium persistent. Flowers not fragrant.

*Natural flowering season.*—Year-round under greenhouse conditions. In the garden, flowering from spring until fall in Germany. Plants begin flowering about nine weeks after planting.

*Flower size.*—Length: About 8.1 cm. Diameter: About 8.1 cm. Depth: About 1 cm to 1.5 cm.

*Flower buds.*—Length: About 2 cm. Diameter: About 1.5 cm. Shape: Ovoid. Color: Close to 52B.

*Petals.*—Quantity/arrangement: Five per flower in a single whorl. Length, banner petal: About 2.9 cm to 3.1 cm. Length, lateral petals: About 3.1 cm. Length, lower petals: About 3.2 cm. Width, banner petal: About 5 cm. Width, lateral petals: About 3.4 cm to 3.6 cm. Width, lower petals: About 4 cm to 4.2 cm. Shape: Cordate. Apex: Emarginate; rounded. Base: Acute to attenuate. Margin: Entire. Texture, upper and lower surfaces: Smooth, glabrous. Color: When opening, upper surface; 52B; towards the margins, 52A. When opening, lower surface: Between 50B and 52C. Fully opened, upper surface: 52B; towards the margins, between 52A and 52B; towards the base, between 56D and 155D; eye zone, 61C. Color becoming closer to between 65D and 155D with development. Fully opened, lower surface: Between 50B and 52C; color becoming close to 56D.

*Sepals.*—Quantity/arrangement: Three; one modified into an elongated spur. Length: About 1 cm. Width: About 5 mm. Shape: Oval. Apex: Acute. Base: Obtuse. Margin: Entire. Texture, upper and lower surfaces: Smooth, glabrous. Color, upper and lower surfaces: Close to 147C. Spur length: About 5.5 cm to 6 cm. Spur diameter: At flower, about 3 mm; at apex, less than 1 mm. Spur texture: Smooth, glabrous. Spur color: 53C.

*Peduncles.*—Length: About 6.5 cm. Diameter: About 2 mm. Angle: Upright to outward. Strength: Strong; flexible. Texture: Smooth, glabrous. Color: 47A.

*Reproductive organs.*—Stamens: Quantity: Five fused at anthers; filaments free. Anther diameter: About 6 mm to 7 mm. Anther color: 52B to 52C. Pollen amount: Moderate. Pollen color: Close to 11D. Pistils: Quantity per flower: One. Pistil length: About 7 mm. Stigma shape: Star-shaped. Stigma color: 4D. Style color: 4D. Ovary color: 183A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate temperatures ranging from about 5° C. to about 35° C.

It is claimed:

1. A new and distinct *Impatiens* plant named 'Fisnics Salice' as illustrated and described.

* * * * *

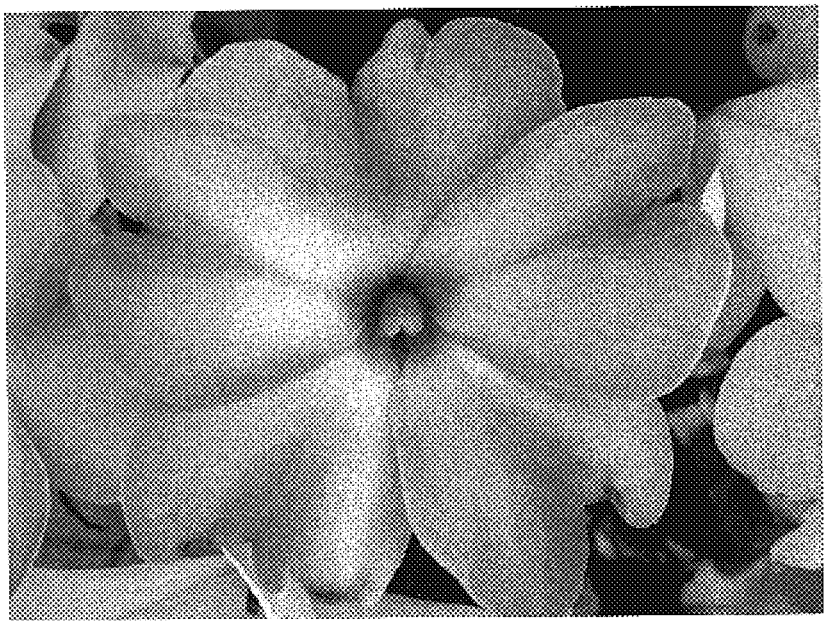

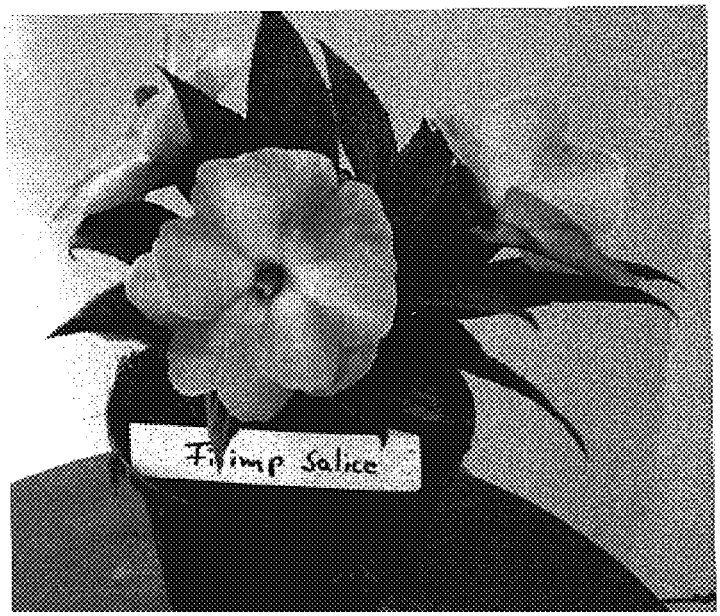
Fifimp Salice